United States Patent [19]

Karami

[11] 3,948,268
[45] Apr. 6, 1976

[54] TAPE FASTENER FOR DISPOSABLE DIAPER

[75] Inventor: Hamzeh Karami, Crystal Lake, Ill.
[73] Assignee: Colgate-Palmolive Company, New York, N.Y.
[22] Filed: Feb. 24, 1975
[21] Appl. No.: 552,585

[52] U.S. Cl. .................. 128/287; 24/67 R; 128/284
[51] Int. Cl.² ................. A41B 13/02; A61F 13/26
[58] Field of Search .......... 128/284, 286, 287, 296; 24/67 R, 67 AR

[56] References Cited
UNITED STATES PATENTS

| | | | |
|---|---|---|---|
| 3,620,217 | 11/1971 | Gellert | 128/284 |
| 3,746,937 | 3/1972 | Gellert | 128/287 |
| 3,776,234 | 12/1973 | Hoey | 128/287 |
| 3,810,472 | 5/1975 | Aldinger et al. | 128/287 |
| 3,848,594 | 11/1974 | Buell | 128/284 |
| 3,875,621 | 4/1975 | Karami | 24/67 |

Primary Examiner—Aldrich F. Medbery
Attorney, Agent, or Firm—Powell L. Sprunger

[57] ABSTRACT

A disposable diaper comprising, an absorbent pad assembly having an absorbent pad, opposed first and second surfaces, and at least one side edge. The diaper has a pressure-sensitive tape strip having a first end section secured to the first surface of the pad assembly, and a second securement section extending past the side edge of the pad assembly. The fastener has a sheet having a first surface and a substantially adhesive-free second surface facing the second surface of the pad assembly and having a relatively high affinity for adhesive. The fastener also includes adhesive means intermediate the second surface of the sheet and the second surface of the pad assembly, with the adhesive means being located adjacent one end of the sheet and being spaced from the side edge of the pad assembly to retain the one end of the sheet to the second surface of the pad assembly.

10 Claims, 8 Drawing Figures

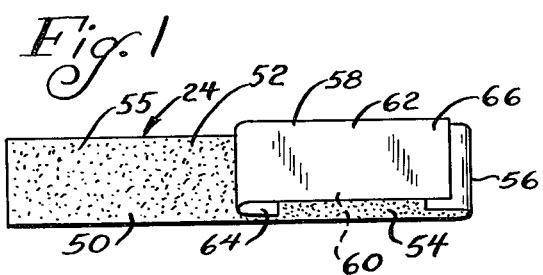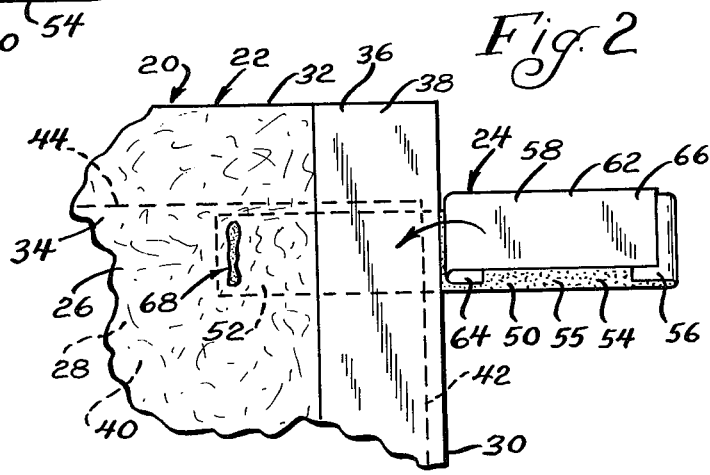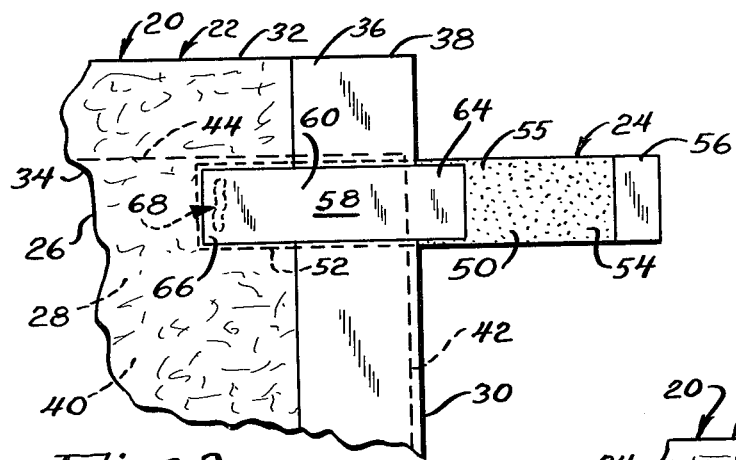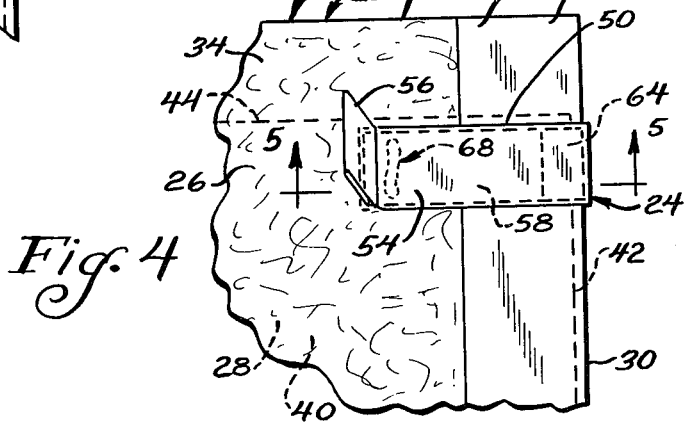

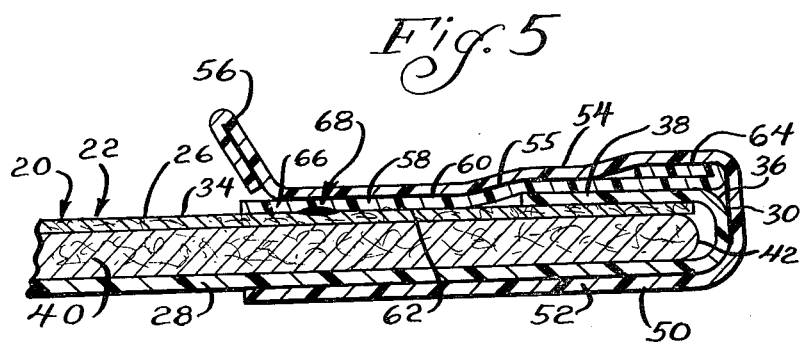
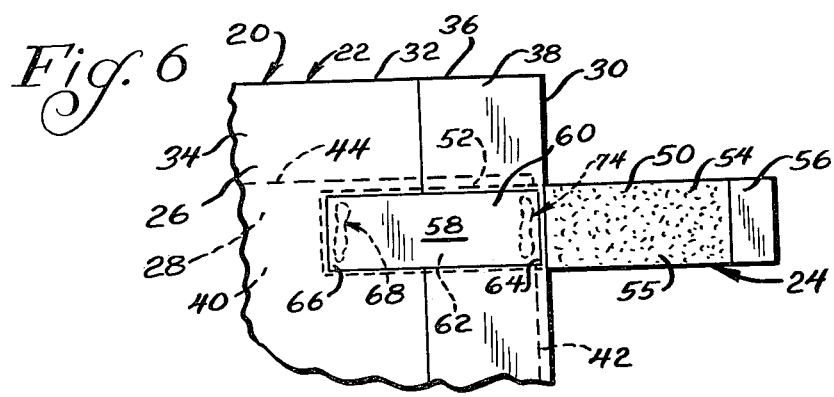
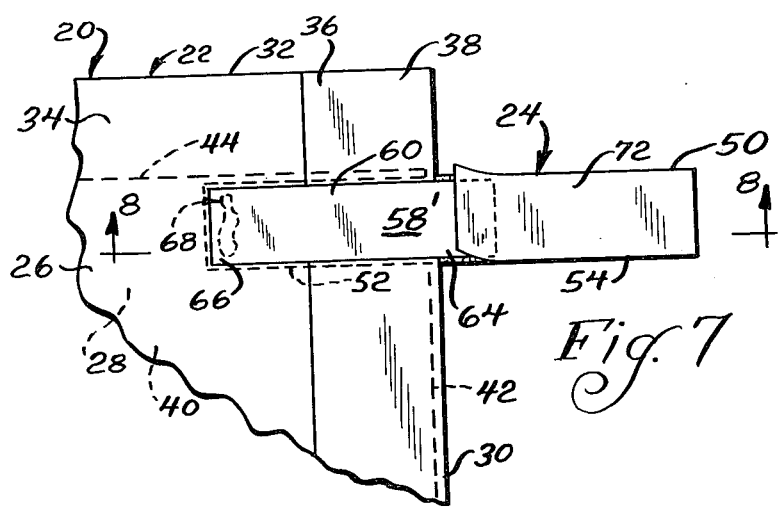
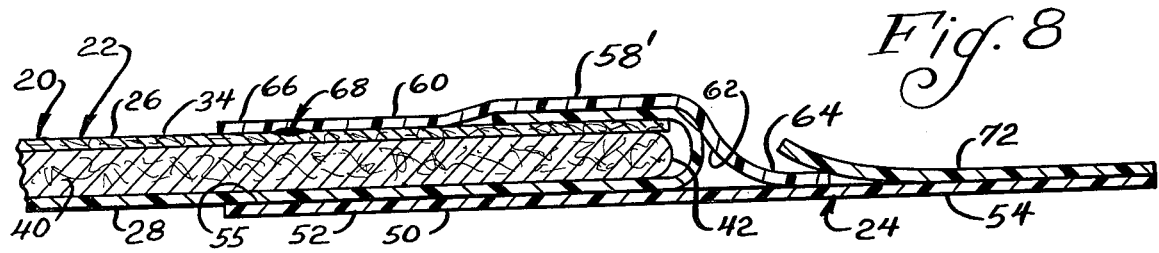

3,948,268

TAPE FASTENER FOR DISPOSABLE DIAPER

BACKGROUND OF THE INVENTION

The present invention relates to absorbent articles, and more particularly to disposable diapers.

A various assortment of disposable diapers have been proposed for use on infants. A number of such diapers have been provided with tape fasteners for securing the diaper about the infant during placement. The tape fasteners have generally taken the form of a tape strip having a securement portion which is covered by a release sheet, with the release sheet being removed from the securement portion of the tape strip during placement of the diaper to expose adhesive on the securement portion. While it has been found that parents prefer that the release sheet be secured to the diaper itself to eliminate the ncesssity for discarding the release sheet, it is also desirable that the tape fastener be made of economic construction to reduce the cost of the diaper to the consumer.

SUMMARY OF THE INVENTION

A principal feature of the present invention is the provision of a tape fastener for a disposable diaper of simplified construction and reduced cost.

The diaper has an absorbent pad assembly having an absorbent pad, a back surface, a front surface, and at least one side edge. The tape fastener comprises, a pressure-sensitive tape strip having a first end section secured to the back surface of the pad assembly, and a second securement end section extending past the side edge of the pad assembly. The tape fastener has a sheet, such as a release sheet, having a first surface which may provide a relatively low affinity for adhesive on the tape strip and having a substantially adhesive-free second surface facing the front surface of the pad assembly, with the second surface having a relatively high affinity for adhesive. The fastener also has adhesive means intermediate the second surface of the sheet and the front surface of the pad assembly, with the adhesive means being located adjacent one end of the sheet and being spaced from the side edge of the pad assembly to retain the one end of the sheet to the front surface of the pad assembly.

In one embodiment, the sheet extends past the side edge of the pad assembly, with the second surface of the other end of the sheet being secured to adhesive on the second end section of the tape strip. In another embodiment, the pad assembly may have second adhesive means adjacent the side edge of the pad assembly and intermediate the sheet and front surface of the diaper to retain the other end of the sheet to the diaper.

Thus, a feature of the present invention is that the sheet is permanently retained against the front surface of the pad assembly, and need not be discarded after placement of the diaper.

Another feature of the present invention is that the sheet is retained against the front surface of the pad assembly by use of a relatively small amount of adhesive additional to that already located on the tape strip.

Thus, another feature of the invention is that the reduced amount of adhesive required to attach the sheet reduces the cost of the diaper.

Still another feature of the invention is that the adhesive free sheet may be secured to the diaper in a simplified manner by high-speed manufacturing equipment.

Yet another feature of the invention is that in one embodiment the other end of the sheet may be located in the region of the side edge of the pad assembly, and the second adhesive means may be omitted to reduce the cost of the diaper.

Further features will become more fully apparent in the following description of the embodiments of this invention and from the appended claims.

DESCRIPTION OF THE DRAWINGS

In the drawings:

FIG. 1 is a perspective view of a tape fastener according to the present invention prior to placement on a diaper;

FIG. 2 is a fragmentary plan view of a disposable diaper showing the tape fastener of FIG. 1 as partially applied to the diaper;

FIG. 3 is a fragmentary plan view of the diaper showing the tape fastener of FIG. 1 as secured to the diaper;

FIG. 4 is a fragmentary plan view of the diaper of FIG. 3 showing a securement portion of a tape strip releasably attached to a release sheet in the tape fastener;

FIG. 5 is a fragmentary sectional view taken substantially as indicated along the line 5—5 of FIG. 4;

FIG. 6 is a fragmentary plan view of a diaper showing another embodiment of the tape fastener of the present invention;

FIG. 7 is a fragmentary plan view of a diaper showing another embodiment of the tape fastener of the present invention; and FIG. 8 is a fragmentary sectional view taken substantially as indicated along the line 8—8 of FIG. 7.

DESCRIPTION OF THE PREFERRED EMBODIMENTS

Referring now to FIGS. 4 and 5, there is shown a disposable diaper generally designated 20 having an absorbent pad assembly 22 and a tape fastener 24 secured to the pad assembly 22. The pad assembly 22 has a front surface 26, a back surface 28, a side edge 30, and an end edge 32 connecting the side edge 30. The pad assembly 22 has a fluid pervious cover sheet 34 defining a substantial portion of the front surface 26 of the pad assembly, a backing sheet 36 defining the back surface 28 of the pad assembly and having a lateral side margin 38 folded over and secured to the front surface 26 of the pad assembly, and an absorbent pad 40 intermediate the cover and backing sheets 34 and 36. The absorbent pad 40 has a side edge 42 preferably located adjacent the side edge 30 of the pad assembly 22, and an end edge 44 connecting the side edge 42 and spaced from the end edge 32 of the pad assembly 22. It is understood that the opposed side of the diaper (not shown) would normally have a structure substantially similar to that described above, and would include a tape fastener as described below.

As shown in FIG. 1, the tape fastener 24 has an elongated pressure-sensitive tape strip 50 having a first end section 52, a second securement end section 54, and adhesive 55 on one surface of the strip. The tape strip 50 may have a folded over end 56 adjacent the outer end of the second end section 54 defining tab means for a purpose which will be described below. The tape fastener 24 also has a release sheet 58 having a first surface 60 providing a relatively low affinity for the adhesive 55 on the tape strip 50, and a second opposed substantially adhesive-free surface 62 having a relatively high affinity for adhesive. The second surface 62 of one end 64 of the release sheet 58 is secured to the adhesive 55 on the second end section 54 of the tape strip 50, while the other end 66 of the release sheet is secured to the front surface 26 of the pad assembly by an adhesive line, as described below. Either the first surface 60 or the second surface 62 of the release sheet 58 may be treated, as desired, to obtain the relative affinities for the adhesive 55. For example, the first surface of a paper strip, serving as the release sheet, may be treated with a silicon release coating to obtain the desired release characteristics from the adhesive, while the second surface remains untreated to obtain a firm bond with adhesive.

As shown in FIG. 2, the first end section 52 of the tape strip 50 is secured to the back surface 28 of the pad assembly 22. As illustrated in FIGS. 2 and 3, the other end 66 of the release sheet 58 is folded over the front surface 26 of the pad assembly 22, with the second surface 62 of the release sheet 58 facing the front surface 26 of the pad assembly. As shown, a line of adhesive 68 intermediate the second surface 62 of the release sheet 58 and the front surface 26 of the pad assembly retains the other end 66 of the release sheet to the pad assembly. The adhesive means 68 extends transversely across the release sheet, and is preferably a hot melt adhesive, such as the adhesive J-4100 sold by H. B. Fuller Co. of St. Paul, Minnesota. Since the second surface 62 of the release sheet 58 has a relatively high affinity for adhesive, the one end 64 of the release sheet 58 is retained by the adhesive on the second end section 54 of the tape strip, while the other end 66 is anchored against the front surface 26 of the pad assembly 22 by the adhesive line 68. Accordingly, the release sheet 58 is retained against the front surface 26 of the pad assembly with a reduced amount of adhesive additional to that on the tape strip 50, thus reducing the cost of the diaper. Additionally, manufacture of the diaper is simplified, since the adhesive-free release sheet may be readily folded over and secured to the diaper by high-speed manufacturing equipment without impediment by an adhesive bearing surface on the sheet.

As shown in FIGS. 3–5, the second end section 54 of the tape strip 50, including the one end 64 of the release sheet 58, is folded over the front of the diaper and the second end section 54 of the tape strip 50 is releasably attached to the first surface 60 of the release sheet 58. Since the first surface 60 of the release sheet 58 has a relatively low affinity for the adhesive on the second end section 54 of the tape strip, the second end section of the tape strip may be readily removed from the release sheet 58 during placement of the diaper. Removal of the second end section 54 from the release sheet 58 is facilitated by the tab 56 at the outer end of the second end section, which is free of attachment to the release sheet 58 or the pad assembly 22. After the second end section 54 of the tape strip 50 is removed from the first surface 60 of the release sheet 58, in the position as shown in FIG. 3, the second end section 54 is properly located for securing the diaper 20 about the infant. Thus, securement of the diaper is accomplished without removal of the release sheet from the pad assembly, eliminating the necessity for separately discarding release sheets after placement of the diaper.

Another embodiment of the present invention is illustrated in FIG. 6, in which like reference numerals designate like parts. In this embodiment, the tape fastener 24 may have a second line of adhesive 74 intermediate the release sheet 58 and the front surface of the pad assembly and located adjacent the side edge 30 of the pad assembly, with the adhesive means 74 extending transversely across the release sheet. In this embodiment, the one end 64 of the release sheet 58 is located adjacent the side edge 30 of the pad assembly 22. Thus, the adhesive line 74 retains the one end 64 of the release sheet against the front surface 26 of the pad assembly 22, while the adhesive line 68 retains the other end 66 of the release sheet 58 against the pad assembly. Accordingly, the release sheet 58 is retained in place against the front surface of the pad assembly by a reduced amount of adhesive. Alternatively, the adhesive line 74 may be omitted from the tape fastener, such that the one end 64 of the release sheet 58 is free from attachment to the diaper. The adhesive line 68 retains the release sheet 58 to the pad assembly with sufficient strength to prevent dislodgement of the release sheet from the diaper while the second end section 54 of the tape strip is peeled from the release sheet in a direction away from the adhesive line 68. Thus, the release sheet remains anchored to the diaper after placement of the diaper about the infant, although a reduced amount of adhesive is used to secure the release sheet to the diaper.

Another embodiment of the present invention is illustrated in FIGS. 7 and 8, in which like reference numerals designate like parts. In this embodiment, a release sheet 72 is releasably attached to the adhesive on the second end section 54 of the tape strip 50. The release sheet 72 is removed from the second end section 54 during placement of the diaper to expose the underlying adhesive which is then used to secure the diaper about the infant. In this embodiment, the sheet 58', which need not have a treated first surface 60, serves to obtain improved anchorage of the first end section 52 of the tape strip 50 to the diaper. The one end 64 of the sheet 58' is secured to the tape strip 50 and the other end 66 of the sheet 58' is attached to the pad assembly, as previously described, thus preventing the first end section 52 of the tape strip 50 from being pulled away from the diaper. The release sheet described in connection with the diaper of FIGS. 1–5 also serves a similar function.

The foregoing detailed description is given for clearness of understanding only, and no unnecessary limitations should be understood therefrom, as modifications will be obvious to those skilled in the art.

I claim:
1. A disposable diaper, comprising:
an absorbent pad assembly having an absorbent pad, opposed first and second surfaces, and at least one side edge; and
a tape fastener comprising,
 a pressure-sensitive tape strip having a first end section secured to the first surface of the pad assembly, and a second securement section extending past said side edge of the pad assembly,
 a sheet having a first surface and a substantially adhesive-free second surface facing the second surface of the pad assembly and having a relatively high affinity for adhesive, and
 first adhesive means intermediate the second surface of the sheet and the second surface of the pad assembly, said adhesive means being located adjacent one end of the sheet and being spaced from the side edge of the pad assembly to retain said one end of the sheet to the second surface of the pad assembly.

2. The diaper of claim 1 wherein said first surface of said sheet has a relatively low affinity for adhesive on the tape strip, and the second section of the tape strip is releasably attached to the first surface of the sheet.

3. The diaper of claim 2 wherein said second section of the tape strip has tab means adjacent its outer end to facilitate removal of the second section from the sheet.

4. The diaper of claim 2 wherein the other end of the sheet is located adjacent said side edge of the pad assembly.

5. The diaper of claim 4 including second adhesive means intermediate the second surface of the sheet and the second surface of the pad assembly, said second adhesive means being located adjacent said other end of the sheet and being spaced from said first adhesive means to retain said other end of the sheet to the second surface of the pad assembly.

6. The diaper of claim 5 wherein said second adhesive means comprises a line of adhesive extending transversely across said sheet.

7. The diaper of claim 1 wherein the other end of said sheet extends past the side edge of the pad assembly, with said other end of the sheet having its second surface secured to adhesive on the second section of the tape strip adjacent said side edge.

8. The diaper of claim 1 including a release sheet releasably attached to the adhesive on the second section of the tape strip.

9. The diaper of claim 1 wherein said first adhesive means comprises a line of adhesive extending transversely across said sheet.

10. The diaper of claim 1 wherein said first adhesive means comprises a hot melt adhesive.

* * * * *